United States Patent [19]

Cartaya

[11] 4,205,126
[45] May 27, 1980

[54] SERUM-FREE CELL CULTURE MEDIA

[76] Inventor: Oscar A. Cartaya, 6 Soldiers Field Park, Apartment 319, Boston, Mass. 02163

[21] Appl. No.: 969,590

[22] Filed: Dec. 14, 1978

Related U.S. Application Data

[63] Continuation-in-part of Ser. No. 951,500, Oct. 16, 1978, abandoned, which is a continuation-in-part of Ser. No. 866,338, Jan. 1, 1978, abandoned.

[51] Int. Cl.$^2$ .............................................. A01N 1/02
[52] U.S. Cl. ....................................................... 435/2
[58] Field of Search ........................................ 195/1.8

[56] References Cited
PUBLICATIONS

Willmer–Cells & Tissues in Culture, vol. 1, (1965), pp. 99–102.

*Primary Examiner*—Sam Rosen
*Attorney, Agent, or Firm*—Robert A. Cesari; John F. McKenna; Andrew F. Kehoe

[57] ABSTRACT

A serum-less medium for use in the growth of cells. The medium is an improved aqueous culture media of the MEM type comprising thyroxin, insulin, and Vitamin A. Hydrocortisone and essential fatty acids may also be advantageously used, as may effective quantities of Vitamin E. Surfactants are used to make the vitamins and any fatty acids available for cell growth. This aqueous media may also comprise cell-growth-enhancing quantities of biotin and folic acids.

13 Claims, No Drawings

SERUM-FREE CELL CULTURE MEDIA

RELATED APPLICATION

This application is a continuation-in-part of application Ser. No. 951,500 filed Oct. 6, 1978 which was a continuation-in-part of application Ser. No. 866,338 filed Jan. 1, 1978, both now abandoned.

BACKGROUND OF THE INVENTION

This invention relates to a novel cell growing medium and novel process for growing living cells.

Over the years there has been a substantial amount of effort directed to the problem of providing a versatile and efficacious culture media from reproducible, fully-characterized components. This "ideal" approach is frequently compromised with respect to the "fully characterized" nature of the components. For example, much work has been done (e.g. as described in U.S. Pat. Nos. 3,128,228 by J. Michl and 3,953,290 by K. Uthne) describing the use of serum of blood fractions in cell culture media. However, these fractions have some of the disadvantages of whole serum and other bulk protein sources. They are not as fully characterized as is desirable; that is, they will differ from batch to batch and introduce unknown variables in the media. Such variables can affect the growth of cells and can do so in wholly umpredictable ways.

Other workers have recognized the value of culture media which is free of serum and other bulk protein supplements which can interfere with cell replication. To date, some of these attempts have proved partially successful. Although the media developed in each case has serious limitations.

Thus, Torney et al in U.S. Pat. No. 3,887,930 and U.S. Pat. No. 4,055,460 describes a media containing a particulate resin which provides an undesirable substrate on which cells can grow and from which their removal can be difficult.

The work described by Bower, Arthur and Fine, Propagation of mouse mammary tumor cell lines and production of mouse mammary tumor virus in a serum free media, in In Vitro (Pages 558–563, Volume 12, No. 8, 1976), utilizes a media containing considerable amounts of ethyl alcohol and lipids. The high volatility of ethyl alcohol (much higher than that of the acqueous media), which is used in this media to disperse the lipids in the acqueous solution, predisposes their media to serious problems. Gradual evaporation of the alcohol must be expected in the conditions to be found in cell culture incubators (about 37° C. with a variable $CO_2$ concentration in the atmosphere), causing their media to separate into a biphasic (lipid-acqueous) mixture. This type of mixture would not be appropriate for most cell culture work, nor would its exact composition be easily regulated. Besides, high concentration of alcohol, by itself, may have undesirable effects upon cell growth in many situations.

Other work, as described by S. T. Donta in "The growth of functional rat glial cells in a serumless medium." in Experimental Cell Research (Pages 119–124, Volume 82, 1973), has succeeded in adapting a single, specialized cell line to grow in a chemically defined media without bulk protein supplementation. However, this media has been unable to support the growth of other cell lines, unless used in combination with albumin. Thus, the mdia is not versatile unless supplemented with proteins which are not fully characterized.

Still another work, as described in U.S. Pat. No. 4,049,494, relates to processes for growing cells in serum-less media wherein the cells are from cell lines which have been specially adapted to function in the media. Such processes and media, of course, are lacking in broad utility. U.S. Pat. No. 4,072,565 describes the use of protamine zinc insulin in processes limited to short-terms by limitations inherent in the media selected.

Therefore, even after one decides on the ideal of providing a serum-free media, it is a further problem to provide a media with a combination of nutrients versatile with respect to a cell type that can be grown in it. Also, these nutrients, once identified, must be made available to the cells in a controlled fashion, without the introduction of highly volatile components of biphasic mixtures of variable composition. Furthermore, such a media must be free of particulate elements which would introduce unwarranted growth surfaces. Finally, this media should not be supplemented with partially refined bulk protein sources.

SUMMARY OF THE INVENTION

It is a principal object of the invention to provide an improved aqueous culture medium for growing cells.

It is a particular object of the invention to provide a culture medium that is fully characterized and, consequently, subject to accurate replication without dependence on animal blood serums or on other non-characterized materials, e.g. the bulk protein supplements commonly used in the art.

A further object of the invention is to provide a culture media described in the foregoing objects which comprises specific combinations of vitamins, fatty acids, and hormones to enhance cellular growth and which is substantially free of volatile or particulate components.

Still another object of the invention is to provide an improved basic culture media, one which is not necessarily optimized with respect to specific nutrients, but which is a substantial improvement over minimum essential media (MEM), including those of the zinc option type, known to the art.

A further object of the invention is to provide cell growth media of improved shelf life and versatility.

Another object of the invention is to provide an improved process utilizing the valuable features of the culture media of the invention.

Further objects of the invention include providing specific combinations of cell-growth materials in such a way as to make them readily available to growing cells over an extended period of time.

Other objects of the invention will be obvious to those skilled in the art on their reading this disclosure.

The above objects have been substantially achieved by (a) the development of an improved basic culture media of the MEM-zinc option type. In the more advantageous forms of the invention, an improved basic media is enhanced with hormones such as thyroxine, and insulin and Vitamin A. It is also advantageous to add hydrocortisone and essential fatty acids such as linoleic, linolenic and arachidonic acids. Vitamin E is also a desirable additive. In each case an acceptably water-dispersable, physiologically-equivalent compound such as physiologically equivalent salts, isomers, homologues, polymers, or other derivatives may be utilized. In general, the physiological equivalents are well known to the art.

It is to be emphasized that the process and media of the instant invention is useful with a wide variety of cells without special selective breeding products to build up a special adaption to the serum. Moreover, the cell growth can be prolonged over periods of three months or more in many advantageous modes of the invention.

The Basic Medium

One basic medium, found advantageous by itself and also advantageous for use as a base for a selective augmentation, is formed with substantial quantities of amino acids, biotin and folic acid. This basic medium, fortified to achieve an improved amino acid profile and fortified with the indicated vitamins, provides a growth culture media of improved versatility and performance.

To form the preferred growth media of the invention, the following are to be added to the fortified basic medium as described above.

Thyroxine: preferably $T_4$ but $T_3$ could also be used. The material is available in many commercial forms, including salt forms. Quantities of $T_4$ from 0.01 to 0.03 micrograms per liter are desirable.

Insulin: A quantity of about 4 milligrams per liter is used.

Hydrocortsone: Again, this material is available in many forms. What is essential is to have a cortisone-active nucleus. A quantity of from about 0.075 to 0.3 milligrams per liter is preferred.

Essential Fatty Acids: The preferred acids are linoleic, linolenic and arachidonic. Although not water soluble, these materials are so emulsified with an appropriate surfactant as to become distributed in the aqueous medium in such a way that their molecules are readily available to the cell-growing population even in the preferred aqueous growth media. A quantity of from about 2.5 to 15 milligrams per liter is required.

Vitamin E and Vitamin A: Vitamin A is preferably used in a quantity of from about 0.1 to 0.4 milligrams per liter. Vitamin E is preferably used in quantities of from about 7.5 to 30 milligrams per liter.

Surfactants: In a sufficient quantity to disperse the Vitamins and fatty acids and, thus, provides means to assure availability of the fatty acids and vitamins to the growing cells. A polysorbate 20 is advantageously used.

It is presently believed that the thyroxin, insulin and Vitamin A should be utilized in all embodiments of the invention. Hydrocortisone and essential fatty acids are highly advantageous. Vitamin E is believed to be important in contributing to the versatility of the invention.

One of the problems with developing a serumless tissue culture media comes with passaging, e.g. transferring, the cells between vessels. Proteolytic enzymes (trypsin or the like) will not be neutralized by this kind of media, since a factor present in serum is active in the neutralization process, and can result in damage or death to the cells. Appropriate physical or mechanical means to detach and passage the cells are, therefore, preferable. If proteolytic enzymes become necessary for whatever reason for effective cell detachment, it is suggested that the cells should be washed before replating in media containing enzyme inhibitors which are commercially available. In any event, it is desirable to avoid cell-damaging quantities of enzymes like trypsin in effecting transfer of these serum-free cell populations.

It is to be understood that the various components of the growth media of the invention can be obtained from natural sources when it is convenient to do so. For example, the fatty acids could be made available as processed vegetable oils, e.g. soybean or safflower oil. In such cases, it is necessary to so process the natural material as to remove any substantial quantities of unknown proteinaceous substances.

Although, it is usually preferable to use a zinc-option-type minimum essential medium (MEM) it is possible to achieve a substantial number of the advantages using the invention by appropriate modification of such commercial products known to those skilled in the art, such as Medium 199 Eagle's Basal Medium, Eagle's Minimum Essential Medium or the like.

Illustrative Examples of the Invention

It is, of course, to be understood that the following examples are intended to be illustrative and that numerous changes can be made in the reactants, precise proportions, and conditions set forth therein without departing from the spirit of the invention as defined in the appended claims.

A fortified basic medium formula is prepared according to good preparatory procedures as known in the art.

| Item | Amount (milligrams per liter) |
| --- | --- |
| L-alanine | 8.9 |
| L-asparagine | 75.0 |
| L-aspartic acid | 13.0 |
| L-glutamic acid | 14.7 |
| L-glycine | 7.5 |
| L-proline | 11.5 |
| L-serine | 52.5 |
| L-arginine HCl | 196.52 |
| L-cystine | 37.2 |
| L-glutamine | 584.0 |
| L-histidine HCl | 65.0 |
| L-isoleucine | 80.88 |
| L-leucine | 160.88 |
| L-lysine | 112.38 |
| L-methionine | 23.30 |
| L-phenyl-alanine | 50.15 |
| L-threonine | 74.18 |
| L-tryptophan | 15.61 |
| L-valine | 71.4 |
| L-tyrosine | 45.9 |
| CaCl | 200 |
| KCl | 400 |
| $MgCl_6H_2O$ | 183 |
| $MgSO_47H_2O$ | 12 |
| NaCl | 6800 |
| $NaH_2PO_4H_2O$ | 150 |
| $NaHCO_3$ | sufficient to adjust to a Ph of 7.4 |
| phenol red | 10 |
| glucose | 2000 |
| Na pyruvate | 110 |
| biotin | 1.0 |
| D-calcium pantothenate | 1.0 |
| choline Cl | 56.0 |
| folic acid | 1.0 |
| inositol | 36.0 |
| nicotinamide | 1.0 |
| pyridoxal HCl | 1.0 |
| riboflavin | 0.1 |
| thiamine | 1.0 |
| $B_{12}$ | 1.36 |
| folinic acid | 1.0 |
| DL thioctic acid | 0.20 |
| putrescine HCl | 0.16 |
| linoleic | 0.084 |
| $FeCl_36H_2O$ | 0.54 |
| $ZnSO_47H_2O$ | 0.14 |
| insulin | 4.00 |

-continued

| Item | Amount (milligrams per liter) |
|---|---|
| HEPES buffer solution | 2380.0 |
| Distilled water to make a total of 1 liter | |

In general, the quantities of ingredients set out above can be modified by about plus-or-minus 20%; which modifications are to be construed to be "about" those required to function as does the listed formula.

HEPES buffer solution is the name given to buffer solutions containing N-2-hydroxyethyl piperazine-N'-2-ethanesulfonic acid. It has a $pK_a$ value of about 7.5.

The aforesaid basic media was used in Example 1 set forth below.

EXAMPLE 1

Table 1C illustrates the advantageous characteristics of this basic medium when it is compared to A. the improved fortified basic media of the invention both with and without the addition of 10% fetal calf serum;

B. a commercially available zinc-option-bearing MEM formula sold under the trade designation IMEMZO & HEPES by Associated Biomedic Systems, Inc., of Buffalo, N.Y. Again, the comparison was carried out with and without augmentation of the formula with 10% fetal calf serum.

The drawing is indicative of the cell growth in terms of thimidine radioactive count (TRC) as follows:

TABLE 1C

| Growth Media and Cell History | Count |
|---|---|
| IMEMZO & HEPES, no serum-cell line | nil |
| IMEMZO & HEPES, no serum initial culture | nil |
| Basic Media of Invention, no serum-initial culture | 1,533 |
| Basic Media of Invention, no serum-cell line culture | 54,672 |
| Basic Media of Invention, serum-cell line culture | 20,825 |
| Basic Media of Invention, serum-initial culture | 8,293 |

"Initial culture" is used to define the primary tumor cells. "Cell line" is used to define cells grown on tissue culture flask for a minimum of five passages.

It will be readily seen that the Basic Media of the invention is superior in cell-line culturing procedures, not only to media with different fully-characterized profiles (IMEMZO) but to itself when fetal calf serum is incorporated therein.

The results disclosed in Example 1 were obtained according to the following procedure:

The tumor cells used in this experiment were rhabdomyosarcoma of mice, Balb-C strain, produced in the laboratory by the intramuscular injection of methylcholanthrene in experimental animals. The tumor was observed to form within several weeks of injection. This tumor was subcultured and kept by serial passage within a line of Balb-C mice and in serum supplemented tissue culture media by different researchers.

A suspension of viable cells were injected subcutaneously in Balb-C mice (from Charles River Breeding Labs) in a concentration of 1,000,000 viable cells per injection. Tumor growth was carefully monitored in these mice.

Cells obtained from these tumors may be classified in several different fashions. "Primary tumor cells" define cells obtained by the dispersion of the tumor grown anew, fresh, in a Balb-C mouse. These cells were separated from the tumor, by the use of standard trypsinization techniques. Trypsin was neutralized with serum and the cells were washed before further use. Their viability was assayed by the trypan blue technique. These cells are labelled as "Primary Tumor Cells."

Cell lines were cultured in tissue culture media from these primary tumor cells by using basic media, as described in the body of this disclosure, e.g. Example 1. However, this basic media used to establish the cell lines contained 10% (by volume) of fetal calf serum. Prior to use of these cell lines, the cells were again dispersed by the cold-media technique described below and their viability checked by the trypan blue technique. These cells are referred to herein as "cell lines."

Transferring of the cells between vessels, in multi-passage work is accomplished by adding cold media (about 4° C.) to the flask followed by shaking and dispersion by vortexing. In this way the cells are cold shocked and readily released for transfer way the cells are cold shocked and readily released for transfer to a new vessel and a new passage.

The following procedure is used to test for the activity of the different growth media formulations:

The growth of cells was estimated by the amount of incorporation of radioactively labelled (tritium labelled) thimidine. Thimidine is incorporated by growing cells for the manufacture of DNA. Thus, the amount of radioactivity incorporated into growing cells incubated in radiactively labelled thimidine directly approximates the growth that has taken place within the cell culture. Cells were grown in this fashion using each of stock-IMEMZO and the basic medium of the invention. For each medium, experiments were carried out with media containing 10% (by volume) fetal calf serum and media containing no serum.

Incorporation of radioactively labelled thimidine by primary tumor cells and cell lines grown in stock-IMEMZO media either with or without fetal calf serum supplemenation, is nil or not significantly different than the background radioactive count. Primary cells grown in basic media with no serum supplementation shows an incorporation of 1,533 radioactive counts. Primary cells grown in basic media with 10% fetal calf serum supplementation showed an incorporation of 8,293 counts.

The cell line, as described above, is a primary tumor cell that has been serially grown in vitro for a minimum of 5 passages. A passage being defined as that period of time it takes for the cells to form a monolayer. This is followed by dispersion of this monolayer and reculturing of cell aliguots in a fresh flask.

Testing of the cell lines resulted in markedly different results. The cell line grown in stock-IMEMZO media with or without serum supplementation again was unable to incorporate radioactivity to any appreciable extent. The cell line grown in basic media with no serum supplementation showed an incorporation of 54,672 counts on the average. The cell line grown in basic media supplemented with 10% fetal calf serum showed an incorporation of only 20,825 counts.

In all cases, the cells were incubated for three days at 37° C. in a 5% $CO_2$ atmosphere before they were exposed to radioactively labelled thimidine for 12 hours and then counted again. In each case, quadruplicate culutures of $10^5$ viable cells were carried out by use of a microtiter plate culturing system. These cells were processed for counting with an automatic harvesting machine and counted in a Searle liquid scintillation counter.

The numbers given for incorporation of radio active counts represent the average number of counts per minute per culture, counted by the liquid scintillation apparatus. All the cells present in each culture were harvested and the total radioactive content of the complete population of cells in each culture yielded the radioactive counts expressed above as an average. Each different type of culture (determined by the media used, the cell type and the presence or absence of fetal calf serum in the media) yielded, therefore, its own average count.

The following conclusions may be derived from the experiments above:
1. Stock-IMEMZO, either with or without serum supplementation, is unable to support the growth of these cells in vitro.
2. Basic medium with a 10% fetal calf serum supplementation is better than the same media without serum supplementation in supporting the growth of primary cells in vitro.
3. Basic medium with no serum supplementation supports the in vitro growth of cell lines up to 250% better than basic medium with 10% serum supplementation.

Basic medium without serum supplementation seems to be clearly superior to the same medium with 10% fetal calf serum supplementation in growing cell lines in vitro. Thereby it provides a medium able to sustain cell lines in vitro without the use of serum or other bulk biological products.

To test the ability of the basic medium to sustain the growth of cell lines for extended periods of time, the cell lines described above were grown in basic medium, free of serum supplementation, for a period of five months. The changeover to serumless medium was accomplished gradually, over 2 weeks. The cells were observed to clump initially, but soon afterwards they regained their normal morphology and were observed to form monolayers and grow as well as the control cell lines kept in media supplemented with 10% fetal calf serum. Thus, the basic medium was clearly successful in supporting the growth of these cell lines. At this point it was decided to terminate these experiments with methylcholanthrene induced rhabdomyosarcoma cell lines and to start testing various other cell lines for their growth in this media.

EXAMPLE 2—The Growth Media

To the above basic media were added the following:

| Item | Amount |
|---|---|
| thyroxine | 0.02 micrograms per liter |
| insulin | 4 milligrams per liter |
| hydrocortisone | 1.5 milligrams per liter |
| linoleic acid | 5.0 milligrams per liter |
| linolenic acid | 5.0 milligrams per liter |
| arachidonic acid | 5.0 milligrams per liter |
| surfactant, emulsifier* | 110 milligrams per liter |
| Vitamin E | 20 milligrams per liter |
| Vitamin A | 0.25 milligrams per liter |

The surfactant is a micelle-forming material sold by Supelco Co. under the trade designation Tween 20. The material is characterized by its ability to emulsify, or isolate and expose, molecules of fatty acids in small micelle-type structures thereby making them readily dispersible in aqueous solutions and available to the growing cells. Any other surfactant which achieves this effect with a reasonable concentration and is not otherwise detrimental to cell growth may also be utilized.

The procedure of Example 1 is used to demonstrate the advantage of the above-described culture media. Excellent results are achieved with cell lines.

EXAMPLE 3

The following certified cell lines, all available in the American-type Culture Collection at Rockville, Md., are also advantageously grown in the growth medium of Example 2, and then counted according to the procedure set forth therein:
MRC—Human embryonic lung cell line.
L929—Mouse fibrosarcoma line.
Vero—African green monkey kidney line.

It is also to be understood that the following claims are intended to cover all of the generic and specific features of the invention herein described and all statements of the scope of the invention which might be said to fall therebetween.

What is claimed is:

1. An MEM zinc option medium wherein the amino acid profile is about as follows:

| Item | Amount (milligrams per liter) |
|---|---|
| L alanine | 8.9 |
| L asparagine | 75.0 |
| L aspartic acid | 13.0 |
| L glutamic acid | 14.7 |
| L glycine | 7.5 |
| L proline | 11.5 |
| L serine | 52.5 |
| L arginine HCl | 196.52 |
| L cystine | 37.2 |
| L glutamine | 584.0 |
| L histidine HCl | 65.0 |
| L isoleucine | 80.88 |
| L leucine | 160.88 |
| L lysine | 112.38 |
| L methionine | 23.30 |
| L phenyl-alanine | 50.15 |
| L threonine | 74.18 |
| L tryptophan | 15.61 |
| L valine | 71.4 |
| L tyrosine | 45.9 |

2. An MEM zinc option medium, as defined in claim 1, wherein said medium is augmented with cell growth promoting quantities of biotin and folic acid.

3. A culture media as defined in claim 1 further comprising

| Thyroxine | 0.01 to 0.03 micrograms per liter |
|---|---|
| Insulin | 4 milligrams per liter |
| Hydrocortisone | 0.075 to 0.3 milligrams per liter |
| Essential Fatty Acids | 2.5 to 15 milligrams per liter |
| Vitamin A | 0.1 to 0.4 milligrams per liter |
| Vitamin E | 7.5 to 30 milligrams per liter |
| Surfactants | Sufficient quantity to disperse vitamins and fatty acids. |

4. A culture media as defined in claim 2 further comprising

| Thyroxine | 0.01 to 0.03 micrograms per liter |
|---|---|
| Insulin | 4 milligrams per liter |
| Hydrocortisone | 0.075 to 0.3 milligrams per liter |
| Essential Fatty Acids | 2.5 to 15 milligrams per liter |
| Vitamin A | 0.1 to 0.4 milligrams per liter |

| | |
|---|---|
| Vitamin E | 7.5 to 30 milligrams per liter |
| Surfactants | Sufficient quantity to disperse vitamins and fatty acids. |

5. A culture media as defined in claim 3 wherein said surfactant is a polysorbate 20.

6. A culture media as defined in claim 1 further comprising

| Item | Amount |
|---|---|
| thyroxine | 0.02 micrograms per liter |
| insulin | 4 milligrams per liter |
| hydrocortisone | 1.5 milligrams per liter |
| linoleic acid | 5.0 milligrams per liter |
| linolenic acid | 5.0 milligrams per liter |
| arachidonic acid | 5.0 milligrams per liter |
| surfactant, emulsifier | 110 milligrams per liter |
| Vitamin E | 20 milligrams per liter |
| Vitamin A | 0.25 milligrams per liter |

7. An aqueous culture media for use in cell growth having about the following formula:

| Item | Amount (milligrams per liter) |
|---|---|
| L alanine | 8.9 |
| L asparagine | 75.0 |
| L aspartic acid | 13.0 |
| L glutamic acid | 14.7 |
| L glycine | 7.5 |
| L proline | 11.5 |
| L serine | 52.5 |
| L arginine HCl | 196.52 |
| l cystine | 37.2 |
| L glutamine | 584.0 |
| L histidine HCl | 65.0 |
| L isoleucine | 80.88 |
| L leucine | 160.88 |
| L lysine | 112.38 |
| L methionine | 23.30 |
| L phenyl-alanine | 50.15 |
| L threonine | 74.18 |
| L tryptophan | 15.61 |
| L valine | 71.4 |
| L tyrosine | 45.9 |
| CaCl | 200 |
| KCl | 400 |
| $MgCl_6H_2O$ | 183 |
| $MgSO_47H_2O$ | 12 |
| NaCl | 6800 |
| $NaH_2PO_4H_2O$ | 150 |
| phenol red | 10 |
| glucose | 2000 |
| Na pyruvate | 110 |
| biotin | 1.0 |
| D-calcium pantothenate | 1.0 |
| choline Cl | 56.0 |
| folic acid | 1.0 |
| inositol | 36.0 |
| nicotinamide | 1.0 |
| pyridoxal HCl | 1.0 |
| riboflavin | 0.1 |
| thiamine | 1.0 |
| $B_{12}$ | 1.36 |
| folinic acid | 1.0 |
| DL thioctic acid | 0.20 |
| putrescine HCl | 0.16 |
| linoleic | 0.084 |
| $FeCl_36H_2O$ | 0.54 |
| $ZnSO_47H_2O$ | 0.14 |
| insulin | 4.00 |

| Item | Amount (milligrams per liter) |
|---|---|
| HEPES buffer solution | 2380.0 |
| $NaHCO_3$ | sufficient to adjust to a pH of about 7.4 |

Distilled water to make a total of 1 liter

8. A culture media as defined in claim 7 further comprising

| | |
|---|---|
| Thyroxine | 0.01 to 0.03 micrograms per liter |
| Insulin | 4 milligrams per liter |
| Hydrocortisone | 0.075 to 0.3 milligrams per liter |
| Essential Fatty Acids | 2.5 to 15 milligrams per liter |
| Vitamin A | 0.1 to 0.4 milligrams per liter |
| Vitamin E | 7.5 to 30 milligrams per liter |
| Surfactants | Sufficient quantity to disperse vitamins and fatty acids. |

9. A medium as defined in claims 3, 4, or 8 wherein said essential fatty acids are predominantly comprised of linoleic acid, linolenic acid and arachindonic acid.

10. A medium as defined in claims 1, 2, 7, 3, 4, 8, 5 or 6 wherein said medium is maintaiend substantially free of cell-damaging quantities of proteolytic enzymes.

11. An improved process for growing lines of living cells comprising the steps of growing said cells in a growth medium, through at least two passages, said medium an MEM-zinc-option type medium having about the following amino acid profile:

| Item | Amount (milligrams per liter) |
|---|---|
| L alanine | 8.9 |
| L asparagine | 75.0 |
| L aspartic acid | 13.0 |
| L glutamic acid | 14.7 |
| L glycine | 7.5 |
| L proline | 11.5 |
| L serine | 52.5 |
| L arginine HCl | 196.52 |
| L cystine | 37.2 |
| L glutamine | 584.0 |
| L histidine HCl | 65.0 |
| L isoleucine | 80.88 |
| L leucine | 160.88 |
| L lysine | 112.38 |
| L methionine | 23.30 |
| L phenyl-alanine | 50.15 |
| L threonine | 74.18 |
| L tryptophan | 15.61 |
| L valine | 71.4 |
| L tyrosine | 45.9 |

12. A process as defined in claim 11 wherein said medium comprises effective amounts of additional nutrients as follows:

biotin
folic acid
Thyroxine
Insulin
Hydrocortisone
Essential Fatty Acids
Vitamin A
Vitamin E
Surfactants 13. A process as defined in claims 11 or 12, wherein transfer of cells from one passage to another is primarily effected by use of physical means and without use of cell-harming quantities of proteolytic enzymes.

* * * * *